(12) United States Patent
Lowles et al.

(10) Patent No.: US 9,872,117 B2
(45) Date of Patent: Jan. 16, 2018

(54) DEVICE AND METHOD FOR ADJUSTING AN OUTPUT TO AN AUDIO PORT BASED ON A DETERMINED SENSITIVITY

(71) Applicant: BLACKBERRY LIMITED, Waterloo (CA)

(72) Inventors: Robert William Lowles, Waterloo (CA); Christian Lorenz, Waterloo (CA)

(73) Assignee: BLACKBERRY LIMITED, Waterloo (CA)

( * ) Notice: Subject to any disclaimer, the term of this patent is extended or adjusted under 35 U.S.C. 154(b) by 0 days.

(21) Appl. No.: 15/057,426

(22) Filed: Mar. 1, 2016

(65) Prior Publication Data
US 2017/0257716 A1    Sep. 7, 2017

(51) Int. Cl.
*H04R 29/00*    (2006.01)
*G01N 27/04*    (2006.01)
(Continued)

(52) U.S. Cl.
CPC ........... *H04R 29/001* (2013.01); *G01N 27/04* (2013.01); *G01R 23/02* (2013.01); *G01R 27/02* (2013.01);
(Continued)

(58) Field of Classification Search
CPC ...... H04R 29/001; H04R 1/1041; H04R 1/10; H04R 5/033; H04R 5/04; H04R 2420/01;
(Continued)

(56) References Cited

U.S. PATENT DOCUMENTS

2006/0035382 A1*  2/2006  Shinozaki ............... G01N 24/08
                                                  436/56
2010/0128900 A1*  5/2010  Johnson .................. H03G 3/001
                                                  381/98
(Continued)

FOREIGN PATENT DOCUMENTS

DE      102007032281 A1   1/2009
EP          2028880 A2     2/2009
(Continued)

OTHER PUBLICATIONS

Extended European Search Report dated Jul. 5, 2017, by EPO, re European Patent Application No. 17157784.4. 8 pages.

*Primary Examiner* — Davetta W Goins
*Assistant Examiner* — Kuassi Ganmavo
(74) *Attorney, Agent, or Firm* — Perry + Currier Inc.

(57) ABSTRACT

A device and method for adjusting an output to an audio port based on a determined sensitivity is provided. The device comprises a processor, an audio port, and an electrical measurement device configured to measure electrical properties of an external device plugged into the audio port over a range of frequencies. Using the electrical measurement device, one or more electrical properties of the external device plugged into the audio port are measured at a plurality of frequencies. A sensitivity of the external device is determined using the one or more electrical properties of the external device measured using the electrical measurement device. An output to the audio port is adjusted based on the sensitivity.

14 Claims, 15 Drawing Sheets

(51) Int. Cl.
*G01R 23/02* (2006.01)
*H04R 1/10* (2006.01)
*G01R 27/02* (2006.01)
*H04R 3/00* (2006.01)
*H04R 1/34* (2006.01)
*H04R 5/033* (2006.01)
*H04R 1/20* (2006.01)
*H04R 5/02* (2006.01)
*H03G 1/02* (2006.01)

(52) U.S. Cl.
CPC ............ *H03G 1/02* (2013.01); *H04R 1/1041* (2013.01); *H04R 1/20* (2013.01); *H04R 1/34* (2013.01); *H04R 3/005* (2013.01); *H04R 5/02* (2013.01); *H04R 5/033* (2013.01); *H04R 2420/01* (2013.01)

(58) Field of Classification Search
CPC . H04R 3/005; H04R 1/34; H04R 1/20; H04R 5/02; H03G 1/02; G01N 27/04; G01R 23/02; G01R 27/02
See application file for complete search history.

(56) References Cited

U.S. PATENT DOCUMENTS

| | | | |
|---|---|---|---|
| 2013/0133431 A1* | 5/2013 | Manabe | G01H 11/06 73/649 |
| 2014/0003616 A1* | 1/2014 | Johnson | H04R 29/001 381/74 |
| 2014/0064503 A1* | 3/2014 | Ko | H04R 29/001 381/59 |
| 2014/0177850 A1* | 6/2014 | Quan | H04R 3/007 381/55 |
| 2014/0241535 A1* | 8/2014 | Poulsen | H04R 29/001 381/58 |
| 2014/0376736 A1 | 12/2014 | Liu | |
| 2015/0016624 A1* | 1/2015 | Li | H04R 29/00 381/74 |
| 2015/0230018 A1* | 8/2015 | Wen | H04R 1/1041 381/59 |
| 2015/0280678 A1* | 10/2015 | Teh | H03G 9/14 455/90.2 |

FOREIGN PATENT DOCUMENTS

| | | |
|---|---|---|
| EP | 2224749 A1 | 9/2010 |
| WO | WO-2009010056 A1 | 1/2009 |

\* cited by examiner

DEVICE AND METHOD FOR ADJUSTING AN OUTPUT TO AN AUDIO PORT BASED ON A DETERMINED SENSITIVITY

FIELD

The specification relates generally to audio devices, and specifically to a device and method for adjusting an output to an audio port based on a determined sensitivity.

BACKGROUND

Headsets all tend to have different sensitivities. Hence, when different headsets are inserted into an audio port of a device, often the same output to each headset can result in either sound being barely audible, even when volume at the device is turned up high, or the sound being earsplittingly loud, even when volume at the device is turned down low. In other words, every headset has a different sensitivity (e.g. due to a multitude of design factors). This can create problems for the user, both in terms of their experience using a certain pair of headsets and also in terms of a user's health. For example, if a user was using a pair of low quality headsets issued by an airline, which can have a low sensitivity of about 103 dB-SPL/V, and then swapped them for a pair of high quality, higher sensitivity headsets, for example with a sensitivity of about 124 dB-SPL/V, the user would experience a sound level change of over 20 decibels. According to various standards and recommendations, the maximum exposure time per 24 hours for a 103 dB sound is 7.5 minutes, while the maximum exposure time for a 124 dB sound is a mere 3 seconds. Hence, such differences in headset sensitivities can lead to either sound from the headset being barely audible or dangerous sound levels being played on a headset.

BRIEF DESCRIPTIONS OF THE DRAWINGS

For a better understanding of the various implementations described herein and to show more clearly how they may be carried into effect, reference will now be made, by way of example only, to the accompanying drawings in which.

DETAILED DESCRIPTION

Figure 1:
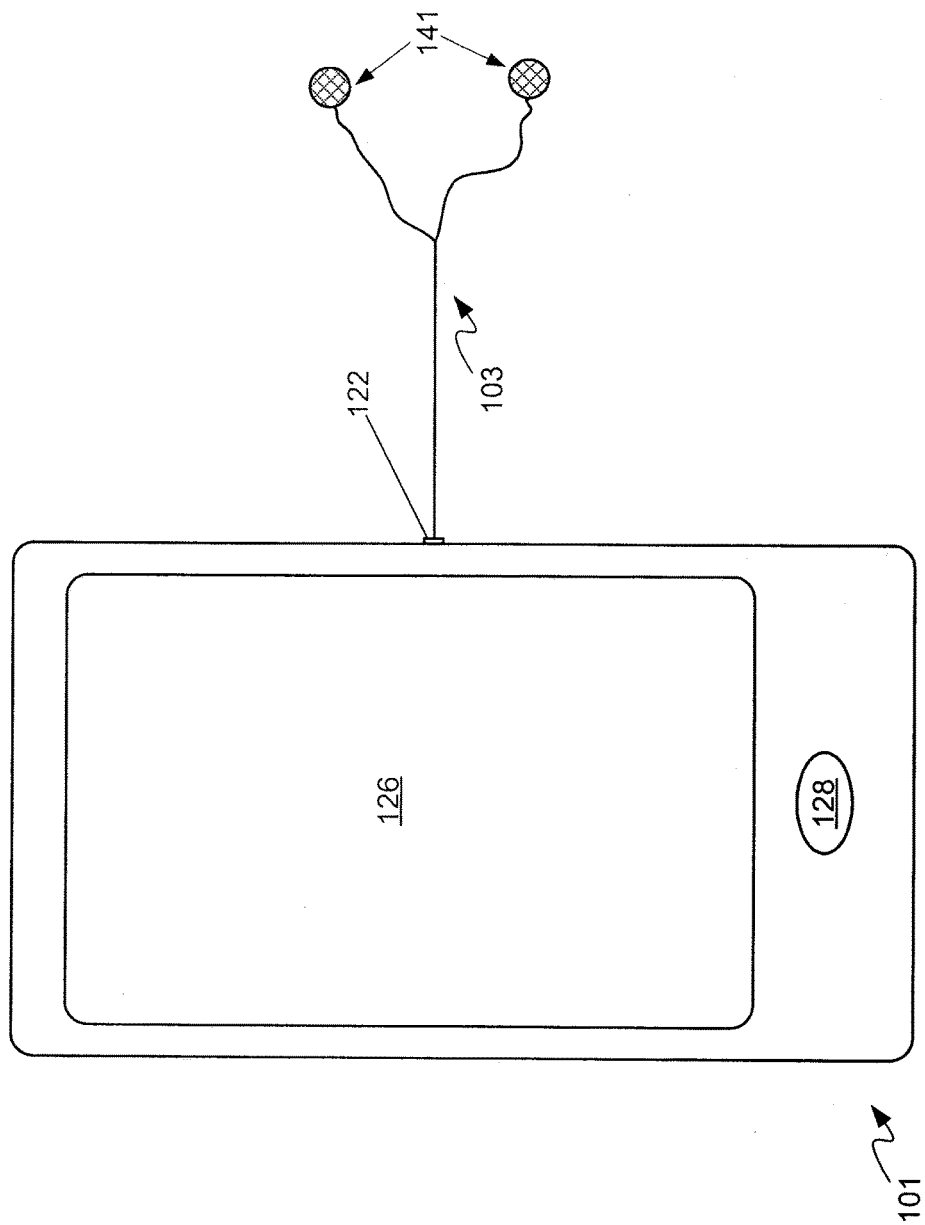
FIG. 1 depicts a front perspective view of a device for adjusting an output to an audio port based on a determined sensitivity, the device mated with an audio headset, according to non-limiting implementations.

In general, this disclosure is directed to a device that includes an audio port that can be mated with an external device, such as an audio headset, and a processor that measures electrical properties of the external device, such as impedance, at a plurality of frequencies to determine sensitivity of the external device. An output at the audio port (e.g. output to the external device) is adjusted based on the determined sensitivity. Specifically, behaviour of various headsets have been studied and a relationship between sensitivity and various electrical properties of the headsets has been determined; hence, in some implementations, impedance of a headset mated with an audio port can be determined at various frequencies and the resistance, inductance and resonance frequency of the headset can be extracted therefrom and used to determine sensitivity. Once the sensitivity has been determined, the output to the audio port (and hence the output to the external device) can be automatically adjusted to either boost the output, in instances where the sensitivity is low, or limit the output, in instances where the sensitivity is high.

In this specification, reference may be made herein to the terms program material, sound data and audio data which can refer to data used to drive a speaker and/or a loudspeaker including, but not limited to, voice data, music data, video data, and the like. In other words program material, sound data and audio data as used interchangeably herein can refer to sound data and/or sound files which can be processed to produce an input to a loudspeaker and/or a speaker. In some instances, the terms program material, sound data and audio data, however, will be used colloquially and interchangeably with the terms input and output, signifying that the program material, sound data and/or audio data is used to produce an input to a loudspeaker and/or an output that drives the loudspeaker, the output comprising an altered version of the input.

In addition, the audio plugs described herein can also be referred to as audio jacks and/or as male connectors and/or as male audio jacks and/or as male audio plugs. Similarly, audio ports described herein can also be referred to as audio sockets and/or as female connectors and/or as female audio ports and/or as female audio sockets.

In this specification, elements may be described as "configured to" perform one or more functions or "configured for" such functions. In general, an element that is configured to perform or configured for performing a function is enabled to perform the function, or is suitable for performing the function, or is adapted to perform the function, or is operable to perform the function, or is otherwise capable of performing the function.

It is understood that for the purpose of this specification, language of "at least one of X, Y, and Z" and "one or more of X, Y and Z" can be construed as X only, Y only, Z only, or any combination of two or more items X, Y, and Z (e.g., XYZ, XY, YZ, ZZ, and the like). Similar logic can be applied for two or more items in any occurrence of "at least one . . . " and "one or more . . . " language.

An aspect of the specification provides a device comprising: a processor, an audio port, and an electrical measurement device configured to measure electrical properties of an external device plugged into the audio port over a range of frequencies, the processor configured to: measure, using the electrical measurement device, one or more electrical properties of the external device plugged into the audio port at a plurality of frequencies; determine a sensitivity of the external device using the one or more electrical properties of the external device measured using the electrical measurement device; and, adjust an output to the audio port based on the sensitivity.

The electrical measurement device can be configured to measure impedance of the external device plugged into the audio port over the range of frequencies, and the processor can be further configured to measure the one or more electrical properties by measuring the impedance of the external device. The processor can be further configured to: extract, from the impedance of the external device, a resistance of the external device, an inductance of the external device, and a resonance frequency of the external device; and determine the sensitivity of the external device using the resistance, the inductance and the resonance frequency.

The device can further comprise a memory storing preconfigured data that relates the sensitivity to electrical properties of external devices, and the processor can be further configured to determine the sensitivity using the preconfigured data. The preconfigured data can relate the sensitivity to: resistance, inductance and resonance frequencies of external devices, and the processor can be further configured to: determine a resistance of the external device, an inductance of the external device, and a resonance frequency of the external device; and determine the sensitivity using the preconfigured data and the resistance, the inductance and the resonance frequency.

The processor can be further configured to initiate measurement of the one or more electrical properties when the external device is plugged into the audio port.

The processor can be further configured to measure the electrical properties of the external device by: playing a first frequency tone at the audio port that is lower than a frequency range of a human hearing system, and measuring a resistance of the external device at first frequency tone; playing a second frequency tone at the audio port that is higher than the frequency range of the human hearing system, and measuring an inductance of the external device at second frequency tone; and playing audio data at the audio port in the frequency range of the human hearing system, and measuring a resonance frequency of the external device in the frequency range of the human hearing system.

The device can further comprise a memory storing a given output level, and the processor can be further configured to adjust the output to the audio port based on the sensitivity such that the output is less than or equal to the given output level.

The processor can be further configured to: play the output at an initial output level while one or more of measurement of the one or more electrical properties and determination of the sensitivity is occurring; and adjust the output to the audio port based on the sensitivity from the initial output level.

The processor can comprise a digital signal processor, the electrical measurement device can comprise a component of an amplifier, and the audio port can comprise one of a 3.5 mm audio plug or a 2.5 mm audio plug.

Another aspect of the specification provides a method comprising: at a device comprising: processor, an audio port, and an electrical measurement device configured to measure electrical properties of an external device plugged into the audio port over a range of frequencies, measuring, using the electrical measurement device, one or more electrical properties of the external device plugged into the audio port at a plurality of frequencies; determining, using the processor, a sensitivity of the external device using the one or more electrical properties of the external device measured using the electrical measurement device; and, adjusting, using the processor, an output to the audio port based on the sensitivity.

The electrical measurement device can be configured to measure impedance of the external device plugged into the audio port over the range of frequencies, and the method can further comprise measuring the one or more electrical properties by measuring the impedance of the external device. The method can further comprise: extracting, from the impedance of the external device, a resistance of the external device, an inductance of the external device, and a resonance frequency of the external device; and determining the sensitivity of the external device using the resistance, the inductance and the resonance frequency.

The device can further comprise a memory storing preconfigured data that relates the sensitivity to electrical properties of external devices, and the method can further comprise determining the sensitivity using the preconfigured data. The preconfigured data can relate the sensitivity to: resistance, inductance and resonance frequencies of external devices, and the method can further comprise: determining a resistance of the external device, an inductance of the external device, and a resonance frequency of the external device; and determining the sensitivity using the preconfigured data and the resistance, the inductance and the resonance frequency.

The method can further comprise initiating measurement of the one or more electrical properties when the external device is plugged into the audio port.

The method can further comprise measuring the electrical properties of the external device by: playing a first frequency tone at the audio port that is lower than a frequency range of a human hearing system, and measuring a resistance of the external device at first frequency tone; playing a second frequency tone at the audio port that is higher than the frequency range of the human hearing system, and measuring an inductance of the external device at second frequency tone; and playing audio data at the audio port in the frequency range of the human hearing system, and measuring a resonance frequency of the external device in the frequency range of the human hearing system.

The device can further comprise a memory storing a given output level, and the method can further comprise adjusting the output to the audio port based on the sensitivity such that the output is less than or equal to the given output level.

The method can further comprise: playing the output at an initial output level while one or more of measurement of the one or more electrical properties and determination of the sensitivity is occurring; and adjusting the output to the audio port based on the sensitivity from the initial output level.

Yet a further aspect of the specification provides a computer-readable medium storing a computer program, wherein execution of the computer program is for: at a device comprising: processor, an audio port, and an electrical measurement device configured to measure electrical properties of an external device plugged into the audio port over a range of frequencies, measuring, using the electrical measurement device, one or more electrical properties of the external device plugged into the audio port at a plurality of frequencies; determining, using the processor, a sensitivity of the external device using the one or more electrical properties of the external device measured using the electrical measurement device; and, adjusting, using the processor, an output to the audio port based on the sensitivity. The computer-readable medium can comprise a non-transitory computer-readable medium.

Figure 2:
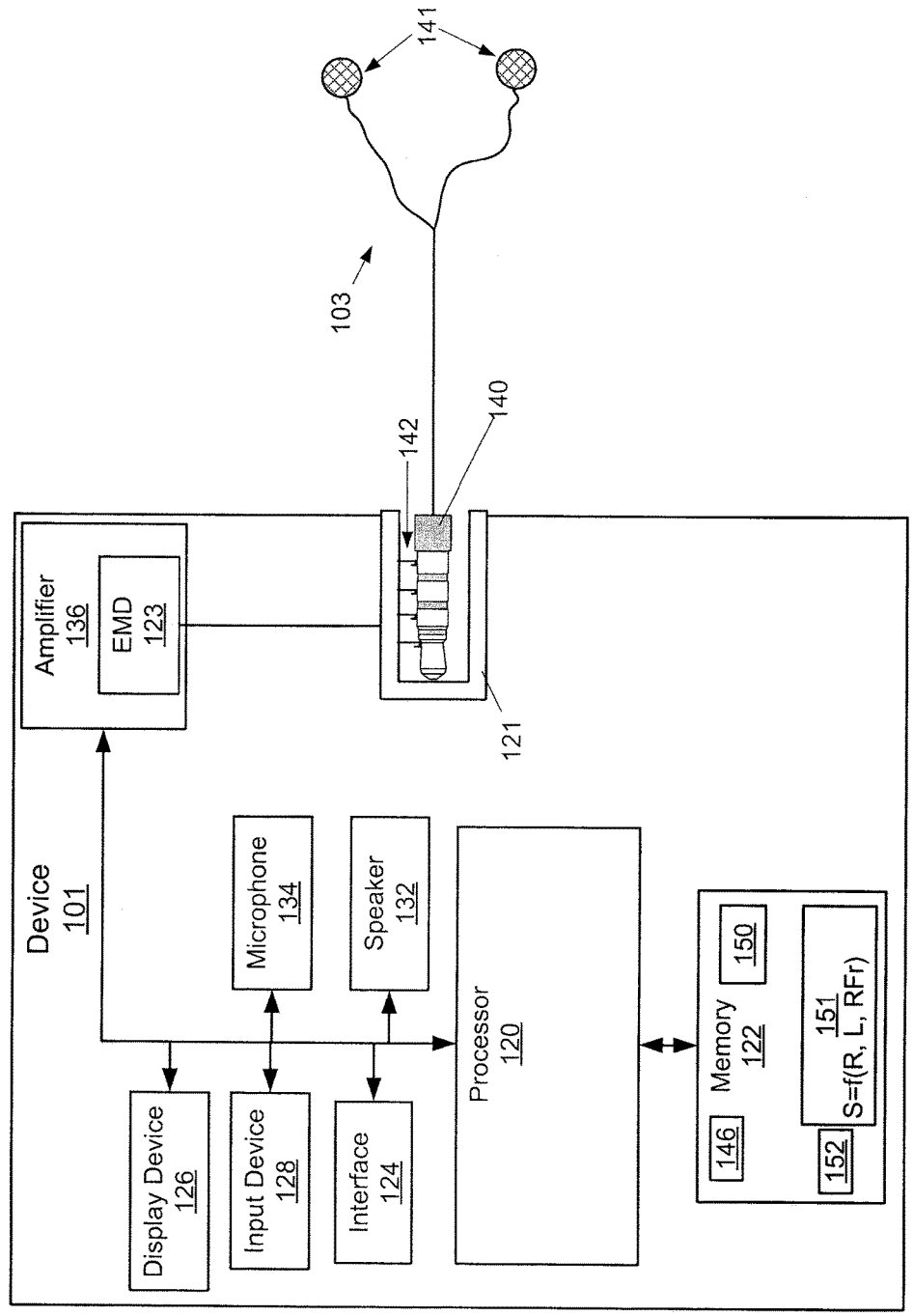
FIG. 2 depicts a schematic diagram of the device and headset of FIG. 1, according to non-limiting implementations.

Attention is next directed to FIG. 1 and FIG. 2 which respectively depict a perspective view and a schematic diagram of a device 101 mated with a headset 103. Device 101 comprises: a processor 120, an audio port 121, and an electrical measurement device (EMD) 123 configured to measure electrical properties of an external device plugged into audio port 121 over a range of frequencies, processor 120 configured to: measure, using electrical measurement device 123, one or more electrical properties of the external device plugged into audio port 121 at a plurality of frequencies; determine a sensitivity of the external device using the one or more electrical properties of the external device measured using the electrical measurement device; and, adjust an output to audio port 121 based on the sensitivity. As depicted, device 101 further comprises: a memory 122, a communication interface (interchangeably referred to as interface 124), a display device 126, at least one input device, a speaker 132 and a microphone 134. Furthermore, as depicted EMD 123 is a component of an amplifier 136, in communication with processor 120; amplifier 136 is generally configured to output audio data, and the like, to audio port 121, and hence to an external device mated with audio port 121, such as headset 103.

As depicted, the external device comprises headset 103, and as depicted in FIG. 2, headset 103 comprises a male audio plug 140 which is removably mated with audio port 121 (e.g. a female audio port). In general, headset 103 further comprises speakers 141 configured for positioning in a human ear; in particular, speakers 141 can comprise earbuds and the like. Device 101 is generally configured to play program material, sound data, audio data, and the like, for example using processor 120, which outputs audio data to audio port 121, using amplifier 136. The audio data is received at audio plug 140 and conveyed to speakers 141, so that the audio data can be used to drive speakers 141. Hence, headset 103 further comprises connections, wires, and the like between audio plug 140 and speakers 141. Also depicted in FIG. 2 are pins 142 in audio port 121 configured to contact complementary contacts at plug 140 to communicate with headset 103 and/or any other external device comprising an audio plug.

For example, headset 103 can be replaced with a set of speakers (e.g. speakers configured to convey sound into a space, a room, etc.), and the like, and/or any external device configured to mate with audio port 121 to receive output from device 101 in order to play sound via speakers. In other words, any external device used with device 101 comprises a plug and/or the like, compatible with audio port 121, as well as one or more speakers.

Device 101, and its components, will now be described in further detail. Device 101 can include, but is not limited to, any suitable combination of electronic devices, communications devices, computing devices, personal computers, laptop computers, portable electronic devices, mobile computing devices, portable computing devices, tablet computing devices, laptop computing devices, desktop phones, telephones, PDAs (personal digital assistants), cellphones, smartphones, e-readers, internet-enabled appliances, mobile camera devices and the like. Other suitable devices are within the scope of present implementations. For example, device 101 need not comprise a mobile communication device, but rather can comprise a device with specialized functions, for example sound functionality.

While a specific physical configuration of device 101 is depicted in FIG. 1, other physical configurations of device 101 are within the scope of present implementations. For example, device 101 can further include video capability, internet connectivity and the like.

Processor 120 can comprise a processor and/or a plurality of processors, including but not limited to one or more central processors (CPUs) and/or one or more processing units and/or one or more digital signal processors (DSPs); either way, processor 120 comprises a hardware element and/or a hardware processor. Indeed, in some implementations, processor 120 can comprise an ASIC (application-specific integrated circuit) and/or an FPGA (field-programmable gate array) specifically configured to implement the functionality of device 101. Hence, device 101 is not necessarily a generic computing device, but a device specifically configured to implement specific functionality including adjusting an output to an audio port based on a determined sensitivity as described in further detail below. For example, device 101 and/or processor 120 can specifically comprise an engine configured to adjust an output to audio port 121 based on a determined sensitivity.

Memory 122 can comprise a non-volatile storage unit (e.g. Erasable Electronic Programmable Read Only Memory ("EEPROM"), Flash Memory) and a volatile storage unit (e.g. random access memory ("RAM")). Programming instructions that implement the functional teachings of device 101 as described herein are typically maintained, persistently, in memory 122 and used by processor 120 which makes appropriate utilization of volatile storage during the execution of such programming instructions. Those skilled in the art recognize that memory 122 is an example of computer readable media that can store programming instructions executable on processor 120. Furthermore, memory 122 is also an example of a memory unit and/or memory module and/or a non-volatile memory.

In particular, memory 122 can store an application 146 that, when implemented by processor 120, enables processor 120 to: measure, using electrical measurement device 123, one or more electrical properties of the external device plugged into audio port 121 at a plurality of frequencies; determine a sensitivity of the external device using the one or more electrical properties of the external device measured using the electrical measurement device; and, adjust an output to audio port 121 based on the sensitivity.

As depicted, memory 122 further stores sound data 150 comprising one or more sound files, and/or multi-media files, and/or program material, and/or voice data, and/or music data and the like, that can be processed by processor 120 to cause amplifier 136 to output audio data to audio port 121 (e.g. to pins 142 of audio port 121 which, in turn, outputs the audio data to headset 103 via audio plug 140).

As depicted, memory 122 further stores preconfigured data 151 relating sensitivity (S) to electrical properties of external devices as described herein, including, but not limited to, headset 103. In particular, preconfigured data 151 can comprise a function that relates sensitivity to resistance (R), inductance (L) and a resonance frequency (RFr) of external devices; in other words, when a resistance, inductance and resonance frequency of an external device can be determined, for example using EMD 123, a sensitivity of the external device can be determined from preconfigured data 151, as described in further detail below.

As depicted, memory 122 further stores given output level 152, and processor 120 can be further configured to adjust the output to audio port 121 based on the sensitivity such that the output is less than or equal to the given output level, as described in further detail below.

In some implementations, preconfigured data 151 and given output level 152 can be incorporated into application 146, while in other implementations one or more of preconfigured data 151 and given output level 152 can be stored separately from application 146. Furthermore, application 146, preconfigured data 151 and given output level 152 can be populated at memory 122 at a factory and/or by downloading application 146, preconfigured data 151 and given output level 152 from an application server and the like.

In addition, at least given output level 152 can be changed (e.g. increased or decreased) via interaction of a user with input device 128, in that a user can select a given output level that is to be output to an external device such as headset 103. Alternatively a maximum given output level (not depicted) can also be stored at memory 122 such that given output level 152 does not exceed the maximum given output level to meet safety standards, for example for headsets. As such, the maximum given output level can be further based on ergonomic sound requirements of headsets and/or external devices.

Processor 120 can be further configured to communicate with display device 126, which comprises any suitable one of, or combination of, flat panel displays (e.g. LCD (liquid crystal display), plasma displays, OLED (organic light emitting diode) displays, capacitive or resistive touchscreens, CRTs (cathode ray tubes) and the like.

Device 101 generally comprises at least one input device 128 configured to receive input data, and can comprise any suitable combination of input devices, including but not limited to a keyboard, a keypad, a pointing device, a mouse, a track wheel, a trackball, a touchpad, a touch screen (e.g. integrated with display device 126), and the like. Other suitable input devices are within the scope of present implementations. In some implementations, one or more of input device 128 and display device 126 can be external to device 101, with processor 120 in communication with any external components via a suitable connection and/or link. As described above, input device 128 can be used to adjust given output level 152 to be increased or decreased such that given output level 152 can be adjusted.

As depicted, device 101 further comprises an optional speaker 132 and an optional microphone 134 (either of which can alternatively be external to device 101). Speaker 132 comprises any suitable speaker for converting audio data to sound to provide one or more of audible alerts, audible communications from remote communication devices, and the like, as well as converting sound data 150 to sounds (e.g. music and the like) at speaker 132 for example when headset 103 is not mated with device 101. Microphone 134 comprises any suitable microphone for receiving sound and converting to audio data. Speaker 132 and microphone 134 can be used in combination to implement telephone and/or communication functions at device 101.

As depicted, processor 120 also connects to optional interface 124, which can be implemented as one or more radios and/or connectors and/or network adaptors, configured to wirelessly communicate with one or more communication networks (not depicted). It will be appreciated that interface 124 is configured to correspond with network architecture that is used to implement one or more communication links to the one or more communication networks, including but not limited to any suitable combination of USB (universal serial bus) cables, serial cables, wireless links, cell-phone links, cellular network links (including but not limited to 2G, 2.5G, 3G, 4G+ such as UMTS (Universal Mobile Telecommunications System), GSM (Global System for Mobile Communications), CDMA (Code division multiple access), FDD (frequency division duplexing), LTE (Long Term Evolution), TDD (time division duplexing), TDD-LTE (TDD-Long Term Evolution), TD-SCDMA (Time Division Synchronous Code Division Multiple Access) and the like, wireless data, Bluetooth™ links, NFC (near field communication) links, WLAN (wireless local area network) links, WiFi links, WiMax links, packet based links, the Internet, analog networks, the PSTN (public switched telephone network), access points, and the like, and/or a combination.

Amplifier 136 generally comprises an audio amplifier configured to receive data from processor 120 and output the data to appropriate pins 142 at audio port 121 to play as sound data at, for example, headset 103 (or any other external device plugged into audio port 121). As disclosed herein, amplifier 136 can be modified to include EMD 123, which can comprise a computer chip configured to measure inductance of an external device as a function of frequency, from which the resistance, impedance and resonance frequency of the external device can be extracted. Alternatively EMD 123 can comprise a computer chip that can measure resistance and impedance as a function of frequency of an external device, from which the resonance frequency of the external device can be extracted. As such, EMD 123 is in communication with appropriate pins 142 of audio port 121 such that such measurements of external devices can be performed. In alternative implementations, EMD 123 can be separate from amplifier 136.

While not depicted, device 101 further comprises a power supply, including, but not limited to, a battery, a power pack and the like, and/or a connection to a mains power supply and/or a power adaptor (e.g. an AC-to-DC (alternating current to direct current) adaptor). In general the power supply powers components of device 101.

Hence, it should be understood that in general a wide variety of configurations for device 101 are contemplated.

Figure 3:
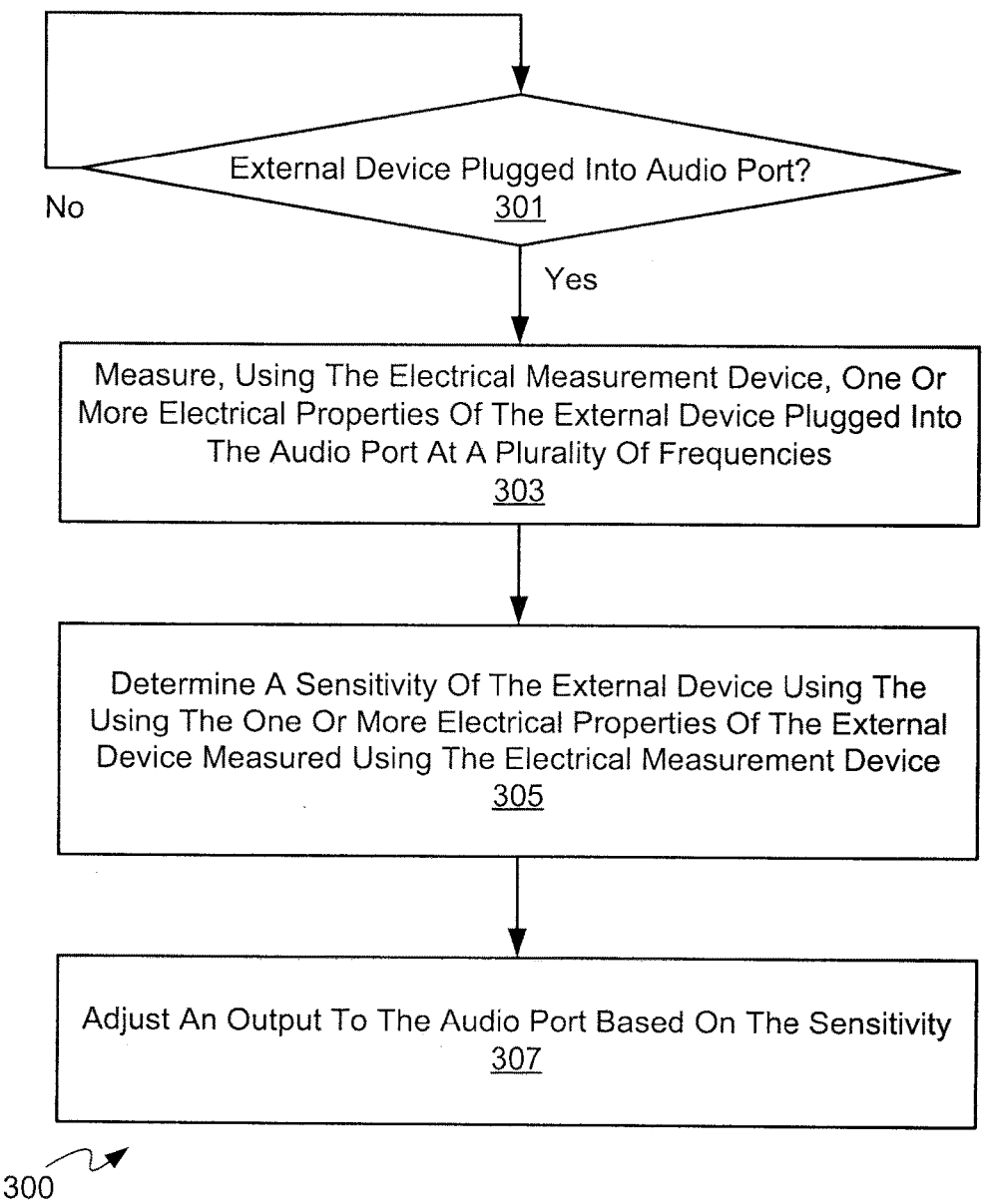
FIG. 3 depicts a schematic block diagram of a method for adjusting an output to an audio port based on a determined sensitivity, according to non-limiting implementations.

Attention is now directed to FIG. 3 which depicts a block diagram of a flowchart of a method 300 for adjusting an output to an audio port based on a determined sensitivity, according to non-limiting implementations. In order to assist in the explanation of method 300, it will be assumed that method 300 is performed using device 101, and specifically by processor 120 and when processor 120 processes instructions stored at memory 122, for example application 146. Indeed, method 300 is one way in which device 101 can be configured. Furthermore, the following discussion of method 300 will lead to a further understanding of device 101, and its various components. However, it is to be understood that device 101 and/or method 300 can be varied, and need not work exactly as discussed herein in conjunction with each other, and that such variations are within the scope of present implementations.

Regardless, it is to be emphasized, that method 300 need not be performed in the exact sequence as shown, unless otherwise indicated; and likewise various blocks may be performed in parallel rather than in sequence; hence the elements of method 300 are referred to herein as "blocks" rather than "steps". It is also to be understood, however, that method 300 can be implemented on variations of device 101 as well.

At an optional block 301, processor 120 monitors whether an external device is plugged into audio port 121; for example, an inductance on one or more pins 142 of audio port 121 can be monitored with EMD 123 and/or amplifier 136 and, when a change in inductance is determined (e.g. a "Yes" decision at block 301), block 303 can be implemented such that processor 120 can be further configured to initiate measurement of the one or more electrical properties when the external device is plugged into audio port 121. Otherwise, block 301 can be repeated (e.g. a "No" decision at block 301) until such a change in inductance is determined.

Alternatively, block 301 may not be implemented and block 303 can occur when, for example, sound data 150 is processed at processor 120 to commence playing sound via audio port 121. In implementations where no external device is plugged into audio port 121, measured electrical properties will generally have values of infinity or zero, and sensitivity can automatically be set to "0" such that no output to audio port 121 occurs regardless of sound data 150 being processed.

At block 303, processor 120 measures, using electrical measurement device 123, one or more electrical properties of the external device plugged into audio port 121 at a plurality of frequencies.

At block 305 processor 120 determines a sensitivity of the external device using the using the one or more electrical properties of the external device measured using electrical measurement device 123.

At block 307 processor 120 adjusts an output to audio port 121 based on the sensitivity.

Hence, for example, processor 120, operating in conjunction with amplifier 136, can output audio data to audio port 121, which is conveyed to headset 103, over a range of frequencies and in particular, frequencies that can be in a range of frequencies audible to human beings and/or in a frequency range of a human hearing system, which are then played by speakers 141. However the frequencies output to headset 103 can be above and below the range of frequencies audible to human beings and/or above and below a frequency range of a human hearing system. EMD 123 is used to measure inductance of headset 103 over the range of frequencies as headset 103 responds to the output thereto.

Figure 4:
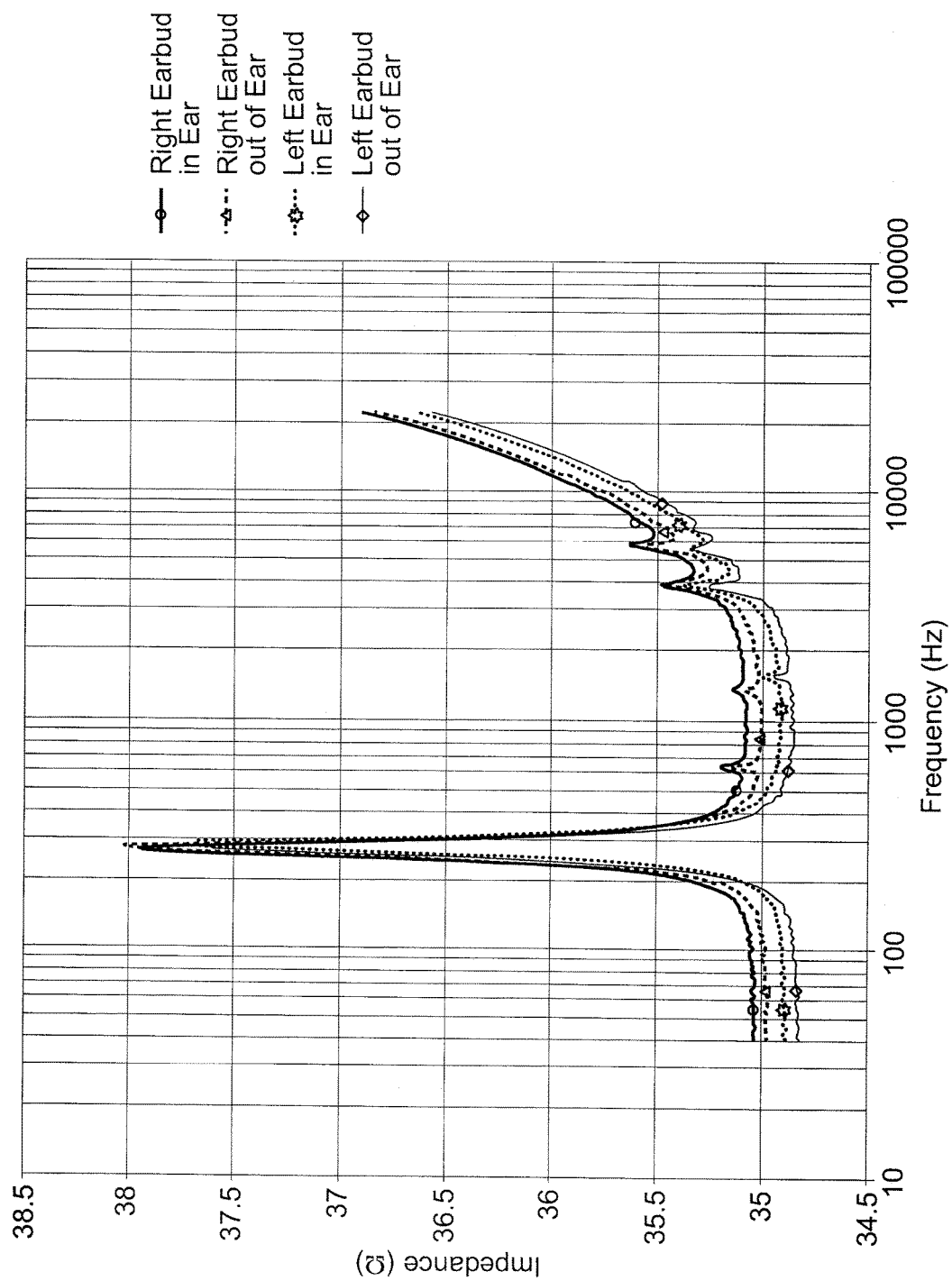
FIG. 4 depicts impedance of earbuds of headset as a function of frequency on a logarithmic scale, under two different conditions, according to non-limiting implementations.

In some implementations, EMD 123 can be configured to measure inductance of an external device mated with audio port 121 over a range of frequencies, and resistance, inductance and resonance frequency can be extracted therefrom. For example, attention is next directed to FIG. 4 and FIG. 5 which depict inductance of right and left earbuds of a given example headset, as function of frequency, under conditions of the earbuds being in and out of a human ear. In FIG. 4, inductance is depicted as function of frequency on a logarithmic scale while in FIG. 5 inductance is depicted as function of frequency on a linear scale.

Regardless, it is clear from at least FIG. 4 that, at lower frequencies (e.g. below about 1000 Hz), impedance generally follows a first trend, other than at resonance frequencies, and at higher frequencies (e.g. above about 2000 Hz), impedance generally follows a second trend; the first trend (e.g. slope) is generally related to resistance of the headset, while the second trend (e.g. slope) is generally related to inductance of the headset. Furthermore, it is clear from both FIG. 4 and FIG. 5 that the impedance response of the headset being measured resonates at a peak around 280 Hz; while there are multiple peaks, the peak at 280 Hz is clearly the largest peak.

Hence, by measuring the impedance of an external device over a range of frequencies, the resistance, the inductance and the resonance frequency of the external device can be determined, for example by extracting the resistance from the lower frequency inductance measurements, extracting the impedance from the higher frequency inductance measurements, and finding a frequency at which a highest peak occurs in the inductance response. The sensitivity of the external device can then be determined using preconfigured data 151 that can relate sensitivity to resistance, impedance and resonance frequency of external devices.

To determine preconfigured data 151, a plurality of headsets (specifically 47 headsets selected randomly) were tested to determine trends in sensitivity of the headsets as a function of resistance, inductance and resonance frequency. For example, attention is directed to FIG. 6, FIG. 7 and FIG. 8 which respectively depict scattered plots of measured sensitivity of the headsets against their measured resistance (FIG. 6), measured inductance (FIG. 7) and measured resonance frequency (FIG. 8). In other words, impedance of each of the headsets was measured as a function of frequency, as in FIG. 4 and FIG. 5, and the resistance, inductance and resonance frequency extracted from the resulting impedance response. In addition, sensitivity of each of the headsets were measured independent of the impedance measurements, using an acoustic measurement system. Furthermore the measurements were conducted in an anechoic chamber.

Figure 6:
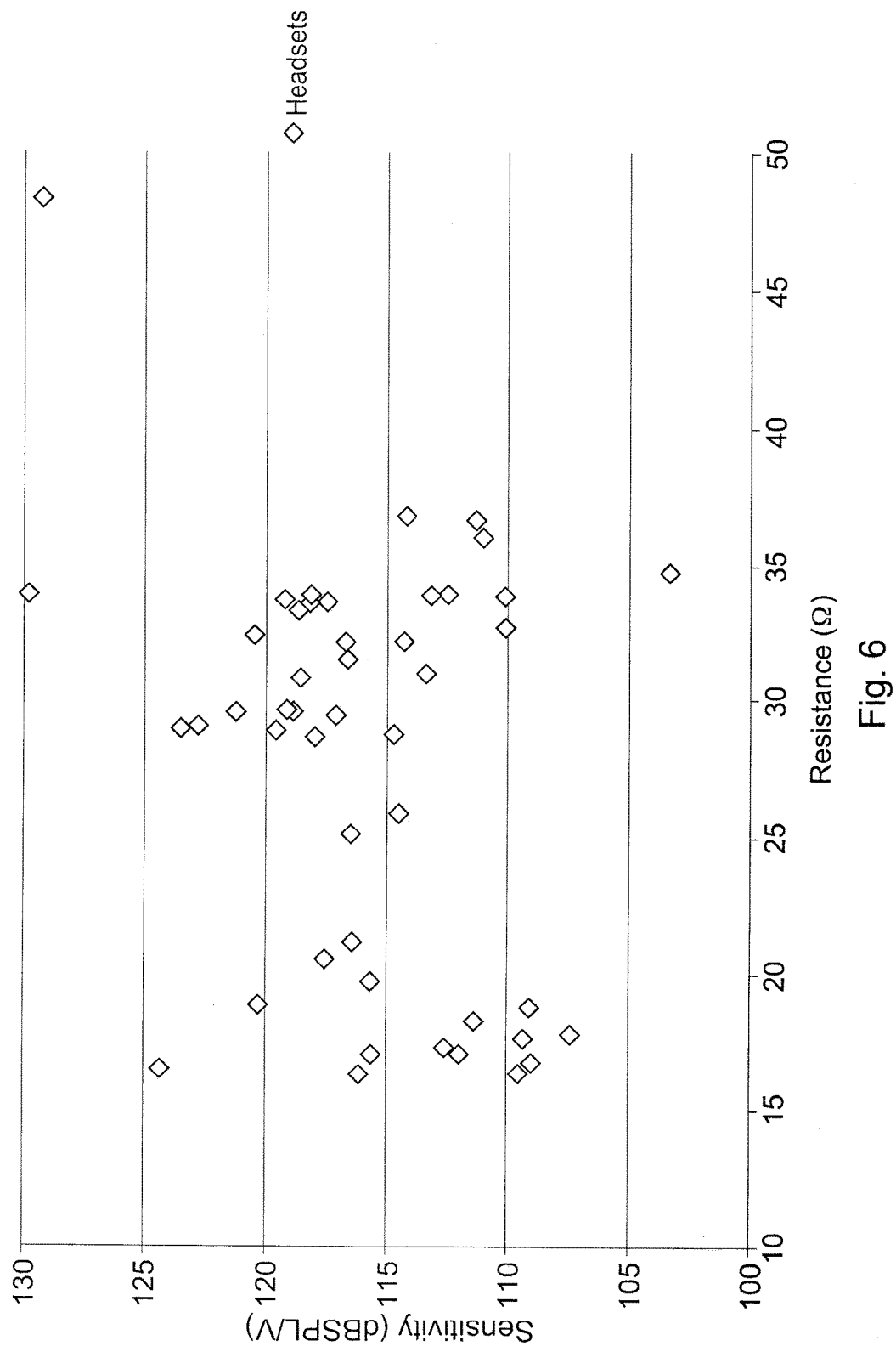
FIG. 6 depicts sensitivity as scatter-plot of measured sensitivities of a plurality of headsets plotted against their measured resistance, according to non-limiting implementations.
Figure 7:
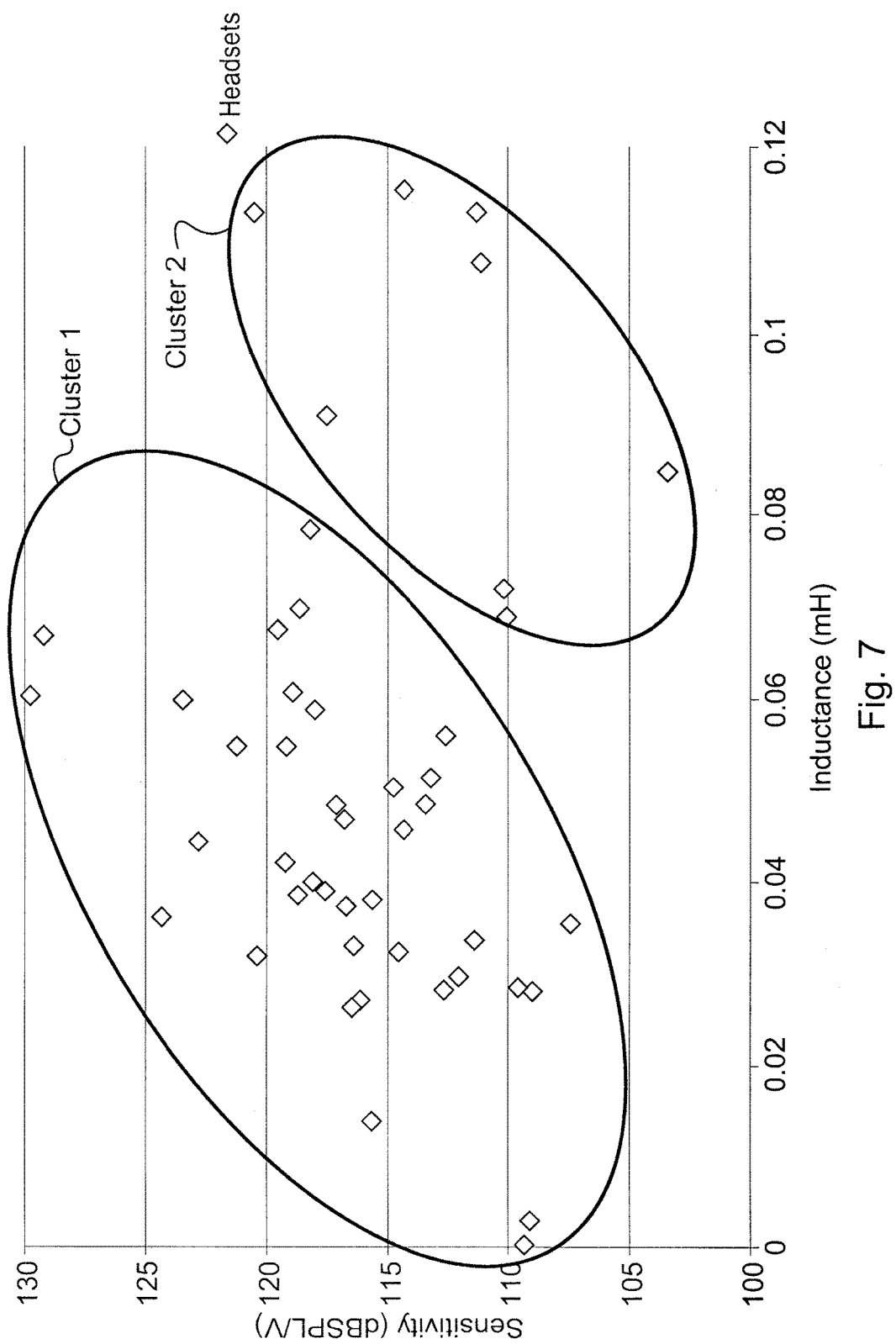
FIG. 7 depicts sensitivity as scatter-plot of measured sensitivities of the plurality of headsets of FIG. 6 plotted against their measured inductance, according to non-limiting implementations.
Figure 8:
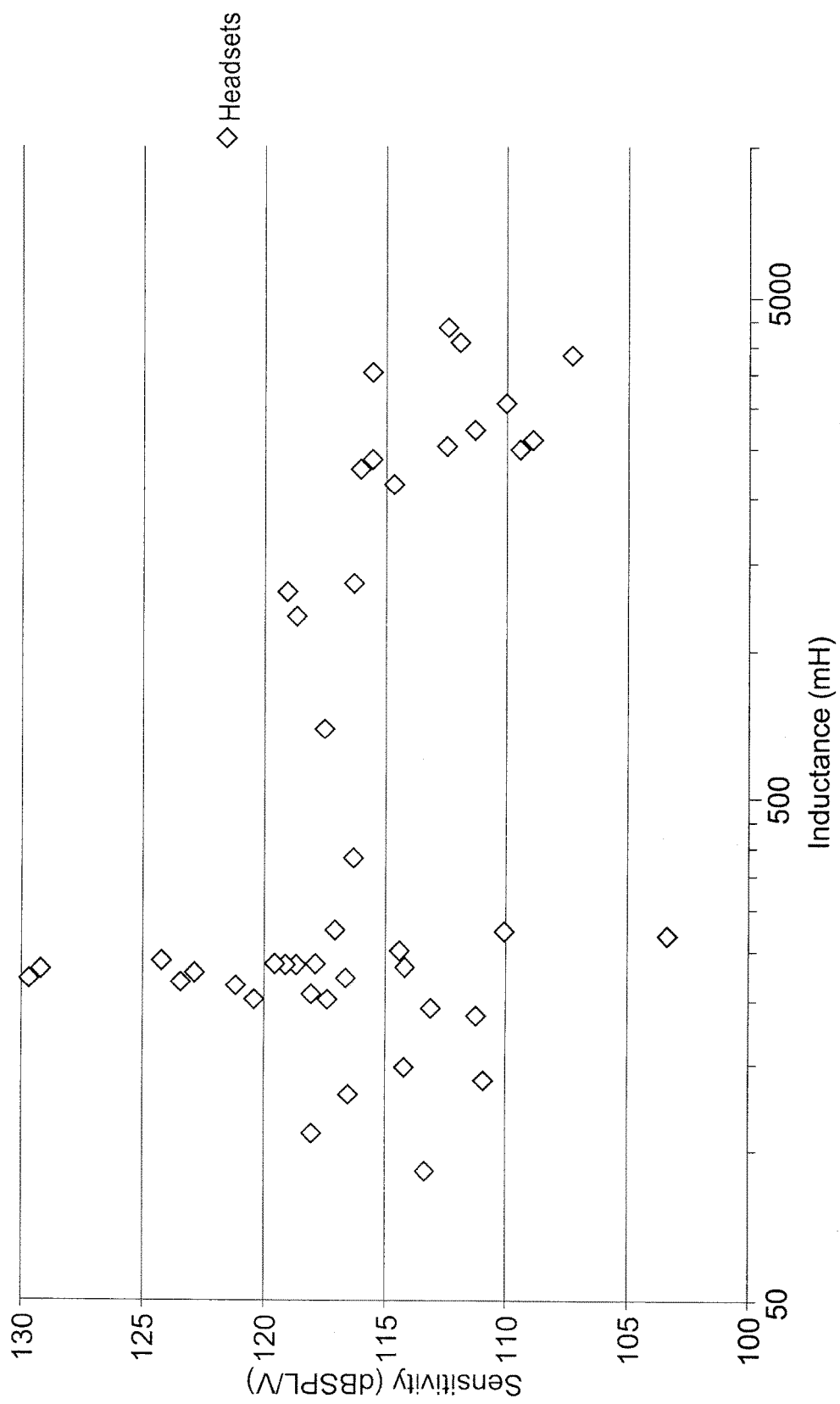
FIG. 8 depicts sensitivity as scatter-plot of measured sensitivities of the plurality of headsets of FIG. 6 plotted against their measured resonance frequencies, according to non-limiting implementations.
Figure 9:
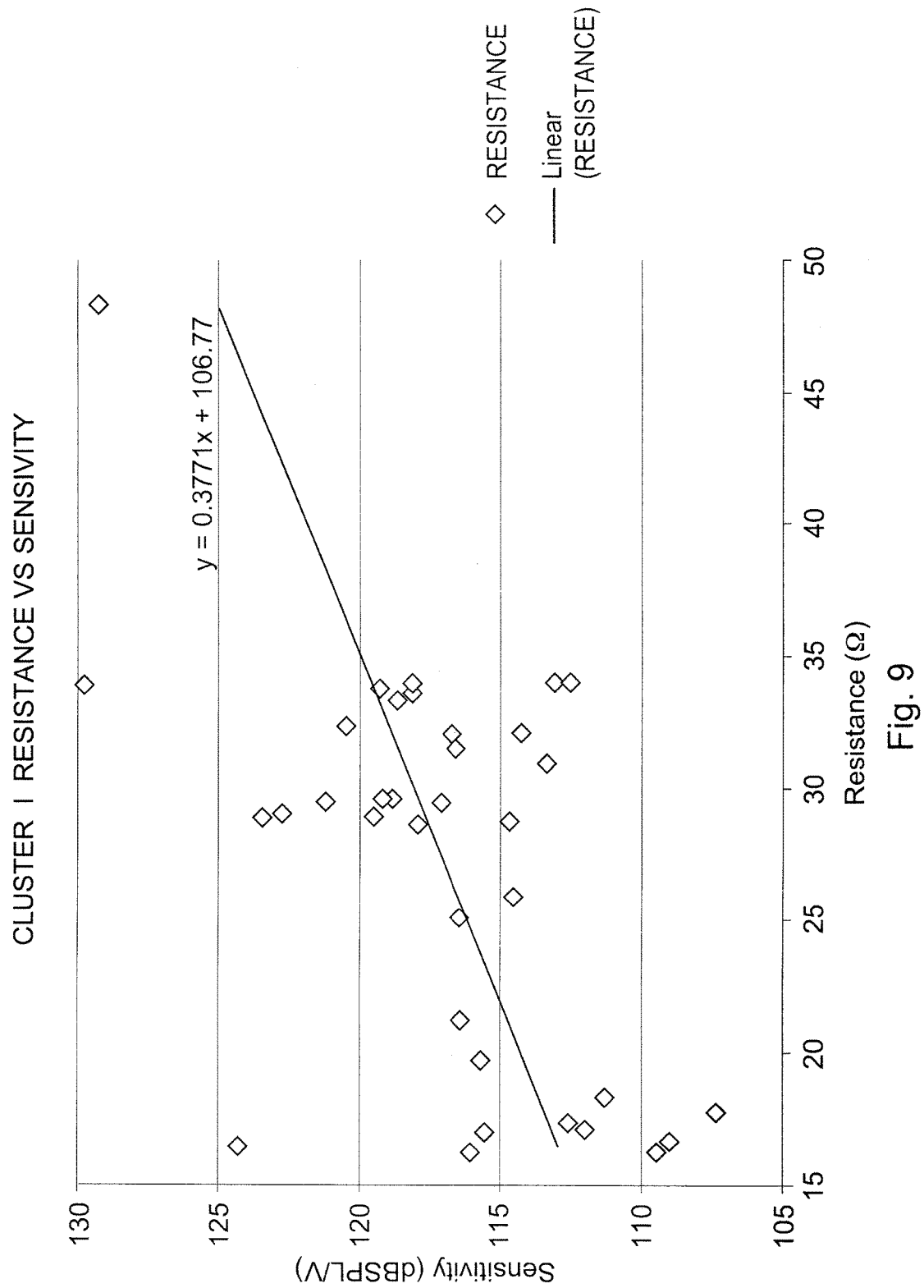
FIG. 9 depicts a linear fit of a portion of the scatter-plot of FIG. 6, according to non-limiting implementations.
Figure 10:
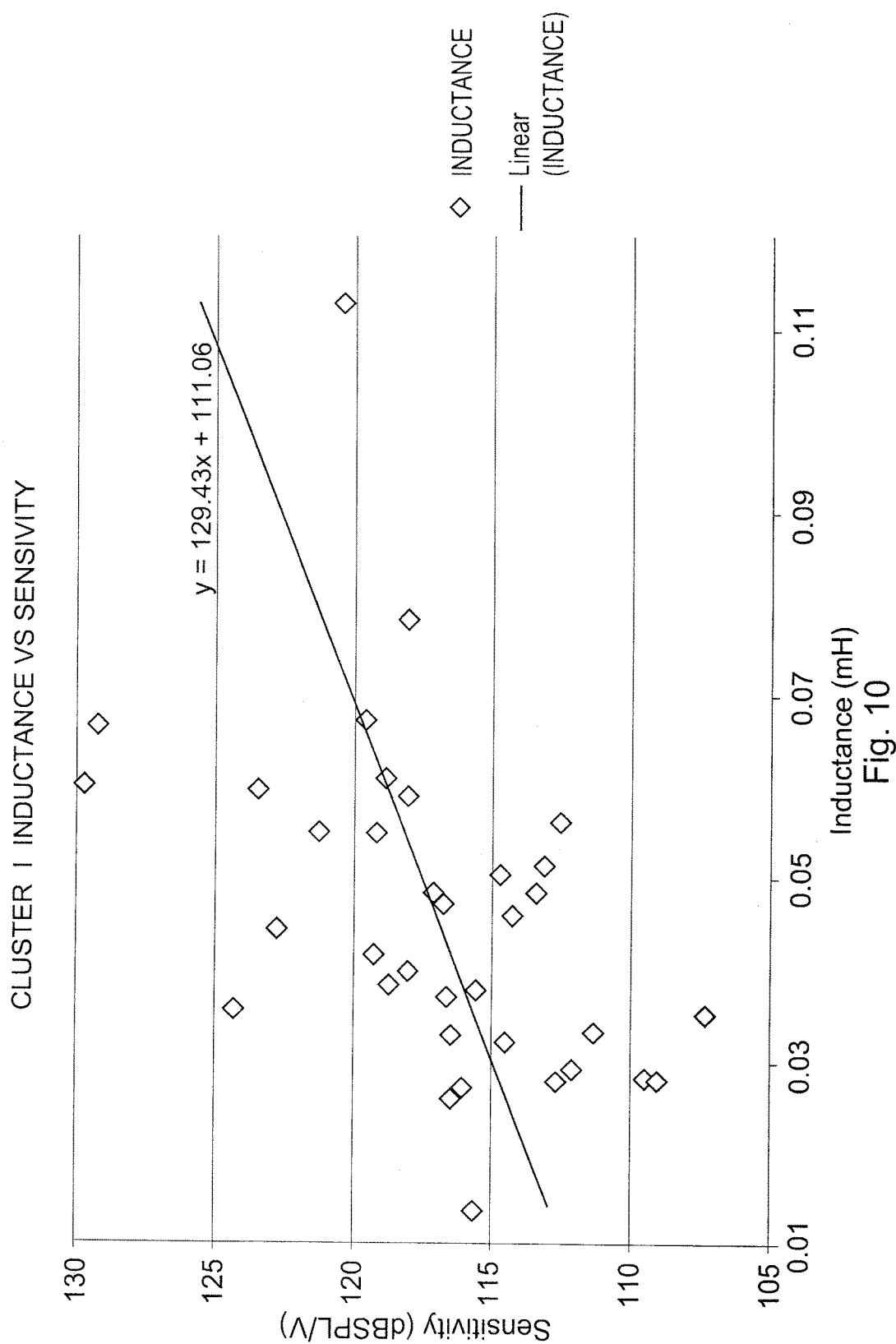
FIG. 10 depicts a linear fit of a portion of the scatter-plot of FIG. 7, according to non-limiting implementations.
Figure 11:
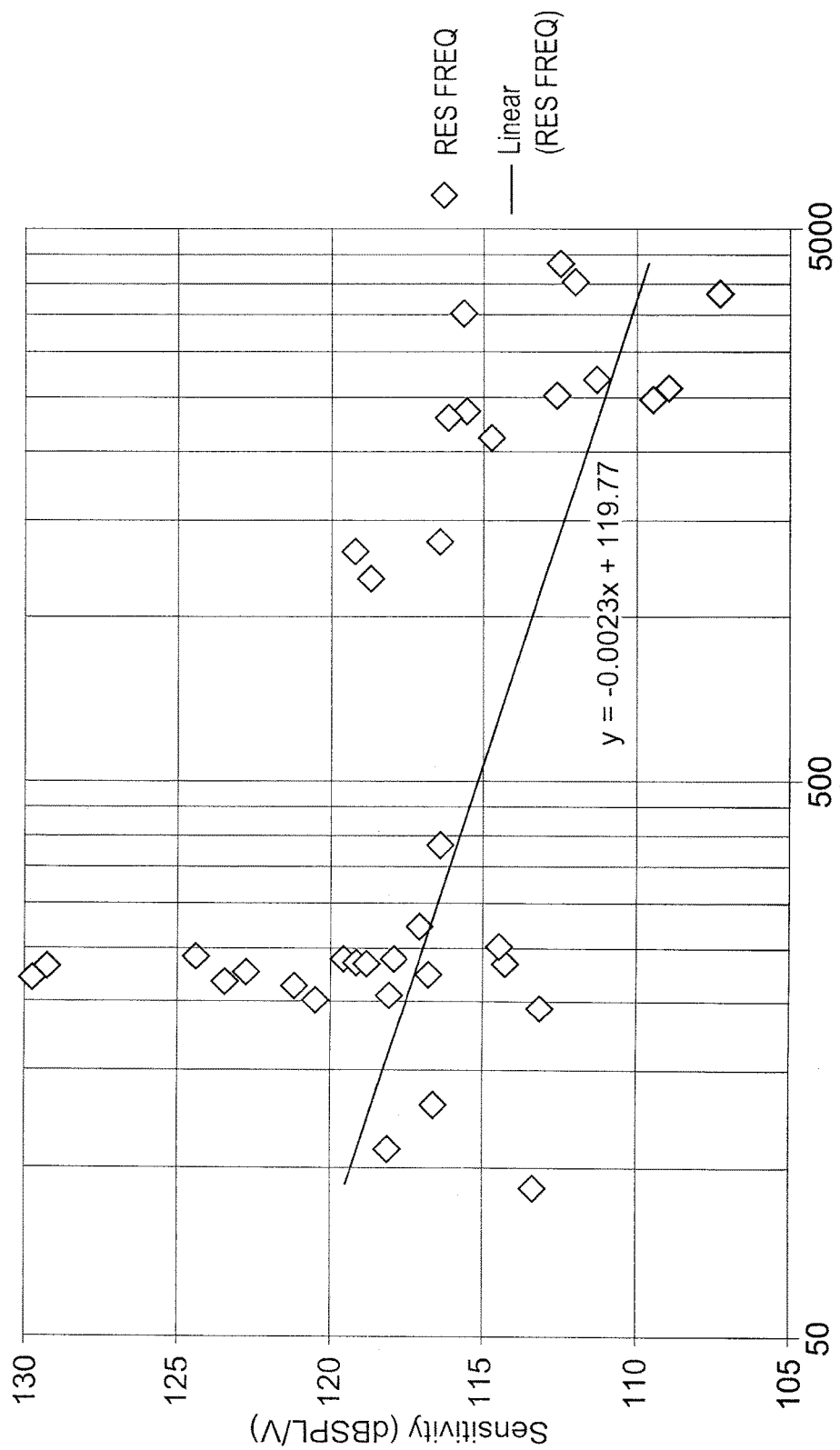
FIG. 11 depicts a linear fit of a portion of the scatter-plot of FIG. 8, according to non-limiting implementations.
Figure 12:
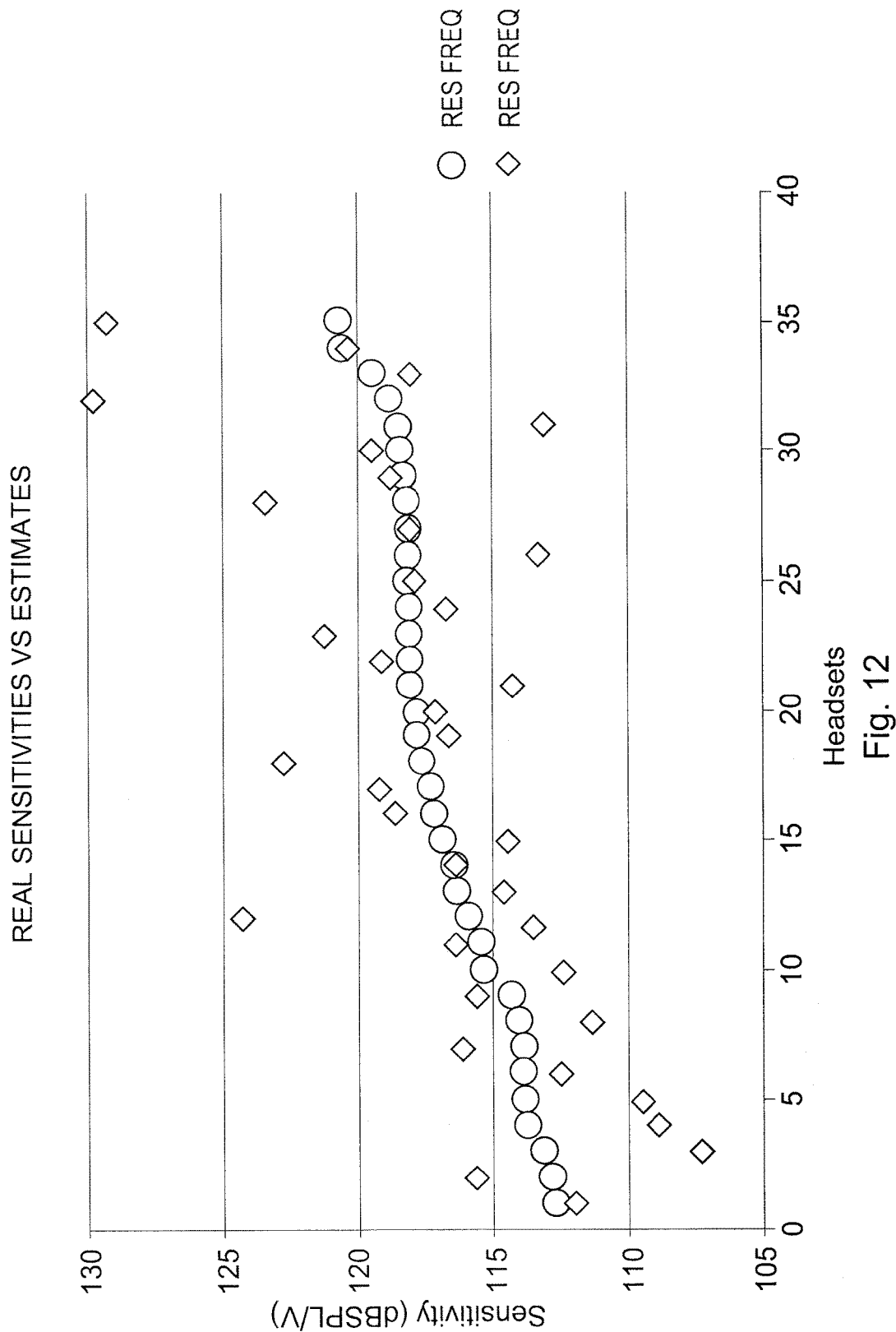
FIG. 12 depicts a comparison between estimated sensitivity and measured sensitivity of a portion of the plurality of headsets, according to non-limiting implementations.

As depicted in FIG. 7, two clusters (e.g. labelled "Cluster 1" and "Cluster 2") of sensitivity vs. inductance were identified and as respectively depicted in FIG. 9, FIG. 10 and FIG. 11, a linear fit of sensitivity as a function of each of resistance, inductance and resonance frequency (respectively based on the scatter plots of FIG. 6, FIG. 7 and FIG. 8) were derived for the first cluster (e.g. "Cluster 1"). The three linear fits were combined into a single equation:

$$S = 0.1257*(R) + 43.1433*(L) - 0.00076668*(RFr) + 112.533 \qquad \text{Equation (1)}$$

In Equation (1), "S" is sensitivity in units of dB-SPL/V (decibel-Sound Pressure Level per Volt), "R" is resistance in Ohms ($\Omega$), "L" is inductance in milliHenry (mH), and "RFr" is resonance frequency in hertz (Hz).

It is further appreciated that Equation (1) can be modified and/or updated based on measurements of yet further headsets. In general, Equation (1) represents a three-dimensional relationship between sensitivity and resistance, inductance and resonance frequency. However, other relationships between sensitivity and electrical properties of external devices can be within the scope of present implementations. In particular, Equation (1) was derived from the specific set of samples (e.g. headsets) characterized that was large enough to be statistically relevant, but is not necessarily completely representative of a complete population of all different available samples and/or headsets. Hence, Equation (1) can be modified and/or become more statistically relevant (e.g. with smaller margins of error) when a larger population of samples and/or headsets are sampled.

In general, there can be two major influences on a relationship between sensitivity and electrical properties of samples and/or headsets:

1. A "best fit" equation (e.g. as represented by Equation (1)) in an x dimensional measurement data space can change and improve prediction precision and tolerance estimate, when more samples of the overall population of the headsets (>>1000) n the world are measured.

2. When measuring further different electrical parameters then the ones referred to above (i.e. by increasing the vector dimensions, e.g. beyond resistance, inductance and resonance frequency), the multidimensional parameter space for clustering increases.

With that, the prediction precision and tolerance estimate of the multidimensional characterization equation can also improve, as shown by experiments performed where two dimensions were initially measured (SPL (sound pressure level) and resistance), then increased to measurement of three dimensions (SPL, resistance and inductance), and then again increased to measurement of four dimensions (SPL, resistance, inductance and resonance frequency). In each instance a sensitivity characterization equation was derived, similar to Equation (1), where the prediction precision and tolerance estimate increased as the dimensionality increased. It is appreciated that the sensitivity characterization equation changed with each parameter/dimension added, as well as with the number of samples measured.

Furthermore, while Equation (1) is particular to headsets, Equation (1) can describe the behaviour of many external devices that can play sound when plugged into audio port 121.

However, in some instances, different types of external devices can behave differently from Equation (1). Hence, in yet further implementations, memory 122 can store a plurality of equations and/or relationships between sensitivity and electrical properties of external devices, which can be similar to Equation (1), with a different equation and/or relationship for different types of external devices. For example, processor 120 can be further determined to classify a given external device plugged into audio port 121 (e.g. based on a measurement of impedance as a function of frequency) and select a given equation and/or relationship appropriately. In a non-limiting example, speaker devices can have a different impedance response from headsets and hence an equation and/or relationship between sensitivity and electrical properties can be determined for speaker devices than for headsets; and, when a speaker device is detected, rather than a headset, the respective equation and/or relationship for speaker devices can be selected from memory 122 to adjust sensitivity. In yet further implementations, an external device can store in a respective memory an identifier thereof (e.g. whether the external device is a headset, a speaker device etc.), which can be retrieved therefrom by processor 120 using audio port 121; processor 120 can then select a respective equation and/or relationship from memory 122 for adjusting sensitivity to the external device (e.g. at block 305 of method 300), once the electrical properties of the external device are measured (e.g. as in block 303 of method 300).

Returning to Equation (1) and the assumption that the external device is a headset, when sensitivity of each headset was calculated and/or estimated from Equation (1) (e.g. using the measured resistance, inductance and resonance frequency of each headset), and compared with measured sensitivity, an average accuracy of about 2.901 dB-SPL/V was found, with a median accuracy of 1.993 dB-SPL/V. While the data from the second cluster ("Cluster 2") were outliers from the estimated sensitivity (e.g. with estimated sensitivity differences being >2.5 dB-SPL/V) in general Equation (1) was found to provide an accurate estimation of sensitivity of a majority of headsets tested. Indeed, further testing showed that a sensitivity majority of tested headsets fell within about +/−5 dB-SPL/V of the sensitivity estimated with Equation (1). Hence, using Equation (1) and determined measured resistance, inductance and resonance frequency of a headset, sensitivity to the headset can be estimated with a reasonable degree of accuracy.

Hence, in device 101, preconfigured data 151 can be populated with Equation (1), such that memory 122 stores preconfigured data 151 that relates the sensitivity to the electrical properties of external devices, processor 120 further configured to determine the sensitivity using preconfigured data 151. For example preconfigured data 151 can be configured at a factory and/or when application 146 is installed at device 101 and/or updated thereafter.

For example as discussed above with reference to Equation (1), preconfigured data 151 can generally relate the sensitivity to: resistance, inductance and resonance frequencies of external devices, and processor 120 can be further configured to: determine a resistance of the external device, an inductance of the external device, and a resonance frequency of the external device; and determine the sensitivity using the preconfigured data and the resistance, the inductance and the resonance frequency.

Furthermore electrical measurement device 123 can be configured to measure impedance of the external device plugged into audio port 121 over a range of frequencies, and processor 120 can be further configured to measure the one or more electrical properties by measuring the impedance of the external device. In these implementations, processor 120 is further configured to: extract, from the impedance of the external device, a resistance of the external device, an inductance of the external device, and a resonance frequency of the external device; and determine the sensitivity of the external device using the resistance, the inductance and the resonance frequency, as described above with reference to FIG. 4 and FIG. 5.

Figure 13:
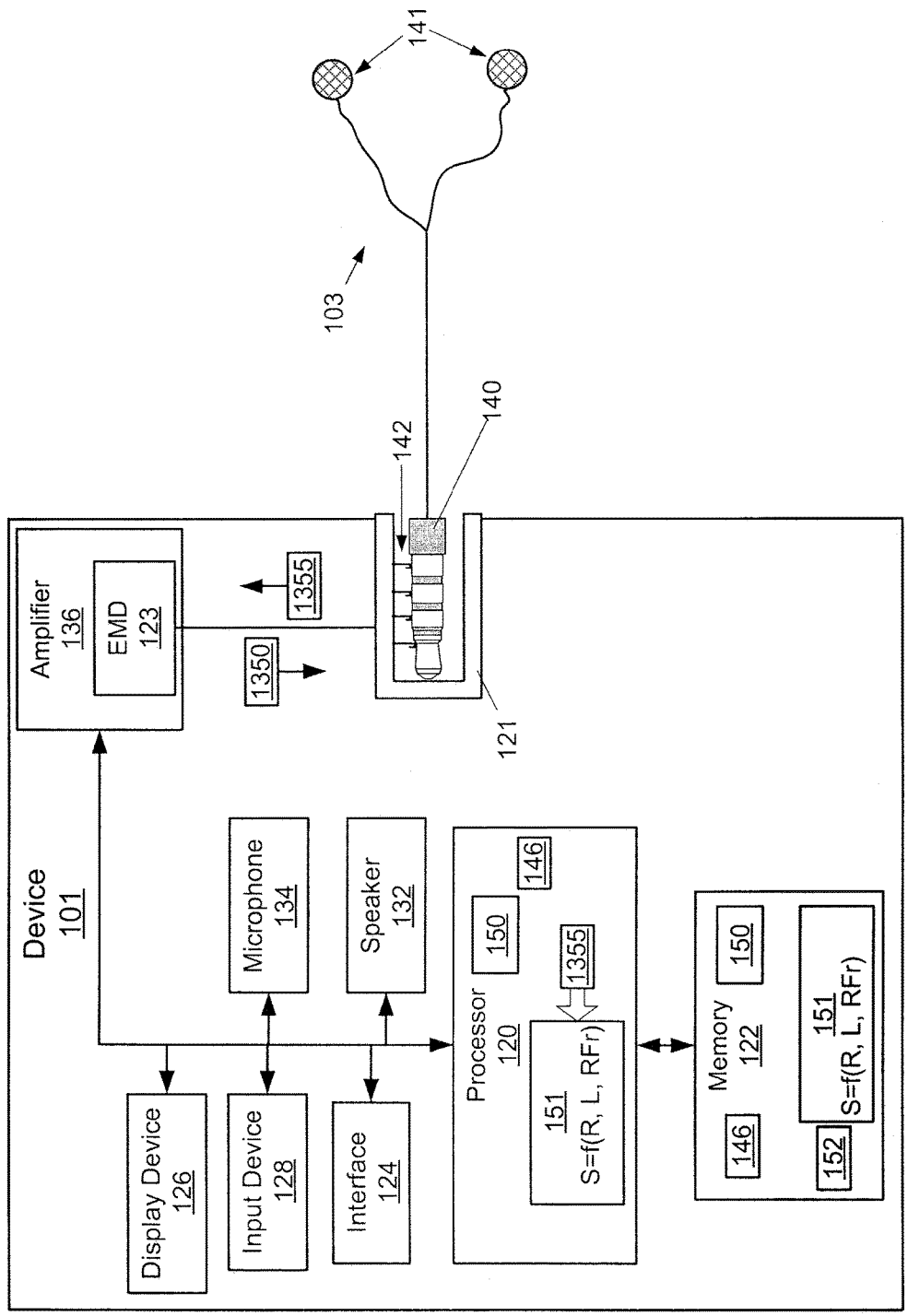
FIG. 13 depicts the device of FIG. 2 implementing a portion of the method of FIG. 3, according to non-limiting implementations.

Attention is next directed to FIG. 13 which is substantially similar to FIG. 2, with like elements having like numbers. In FIG. 13, processor 120 is processing application 146 and, in turn processing sound data 150 to control amplifier 136 to provide an output 1350 to audio port 121, which is conveyed to headset 103, where output 1350 is converted to sound at speakers 141. For example, output 1350 can comprise music data to be converted into sound at speakers at a plurality of frequencies. Furthermore, output 1350 can be played at an initial output level, for example as stored at memory 122 as a last output level of whichever headset was last plugged into audio port 121. Alternatively, the initial output level can be preconfigured at memory 122 to be a value which will not exceed safety levels based, for example on standards and an assumption that the sensitivity of a headset (prior to determination thereof using method 300) is high (e.g. greater than 120 dB-SPL/V).

FIG. 13 further depicts EMD 123 measuring electrical properties 1355 of headset 103 as a function of frequency. In these implementations, no special tones and/or frequencies are output to headset 103; rather, music data, and the like, is output to headset 103 and EMD 123 measures electrical properties of headset 103 on the basis of any frequencies in the music data. Hence, such measurement can be referred to as "passive". Such a measurement further assumes that there are frequencies in the music data that occur over a range that will allow determination of resistance, inductance and resonance frequency of headset 103.

In any event, FIG. 13 also depicts processor 120 receiving electrical properties 1355 (e.g. at block 303 of method 300) and using electrical properties 1355 to determine sensitivity from data 151 (e.g. at block 305 of method 300). For example, from electrical properties 1355, resistance, impedance and a resonance frequency of headset 103 can be determined and Equation (1) used to adjust output 1350 to given output level 152 (e.g. at block 307 of method 300).

Figure 14:
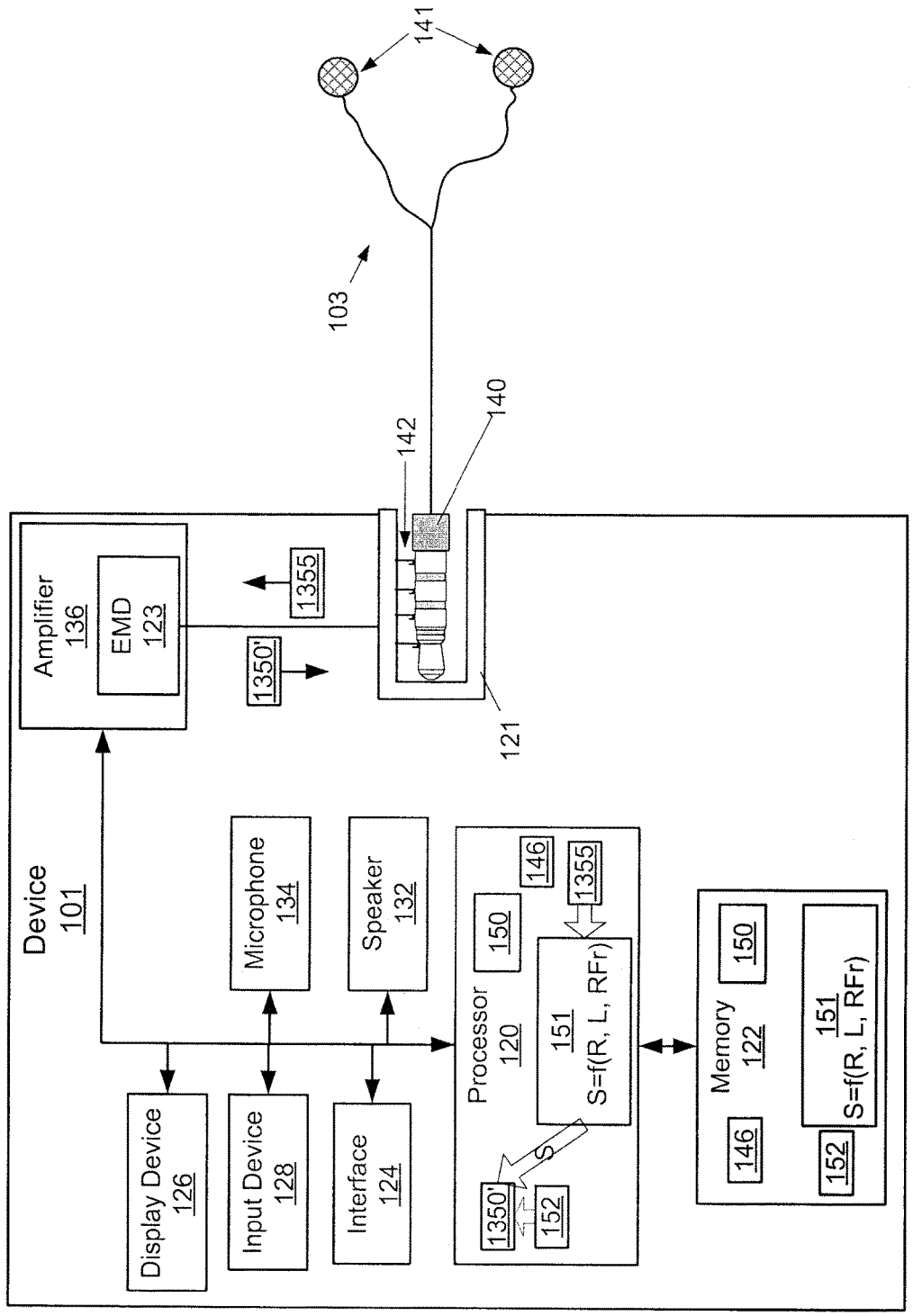
FIG. 14 depicts the device of FIG. 2 implementing a further portion of the method of FIG. 3, according to non-limiting implementations.

Hence, as depicted in FIG. 14, which is substantially similar to FIG. 13, with like elements having like numbers, a sensitivity "S" is determined from electrical properties 1355, and processed with given output level 152 to adjust output 1350 to an output 1350', which can be set to be about equal to given output level 152.

As also depicted in FIG. 14, EMD 123 can continue to measure electrical properties 1355 and when more accurate determinations of resistance, impedance and a resonance frequency of headset 103 are accumulated, sensitivity, and hence output 1350' can be further adjusted. In other words, time-averaged values of each of resistance, impedance and a resonance frequency of headset 103 can be determined and sensitivity and output 1350' adjusted accordingly over time. Hence, if the electrical properties of headset 103 change over time and/or as more data is accumulated; output 1350' can be adjusted accordingly.

Hence, FIGS. 13 and 14 depict that processor 120 can be configured to: play output 1350 at an initial output level while one or more of measurement of the one or more electrical properties and determination of the sensitivity is occurring; and adjust the output (e.g. to output 1350') to audio port 121 based on the sensitivity from the initial output level.

While FIG. 13 and FIG. 14 depict a passive implementation of method 300, in other implementations, an active implementation of method 300 can occur. For example, attention is next directed to FIG. 15 which is substantially similar to FIG. 2, with like elements having like numbers. Specifically, in FIG. 15 (at block 303 of method 300), processor 120 is further configured to measure the electrical properties of the external device by: playing a first frequency tone 1501 at audio port 121 that is lower than a frequency range of a human hearing system, and measuring a resistance 1555-1 of the external device at first frequency tone 1501; playing a second frequency tone 1555-2 at audio port 121 that is higher than the frequency range of the human hearing system, and measuring an inductance 1555-2 of the external device at second frequency tone 1502; and playing audio data 1550 at audio port 121 in the frequency range of the human hearing system, and measuring a resonance frequency 1555-3 of the external device in the frequency range of the human hearing system.

Figure 15:
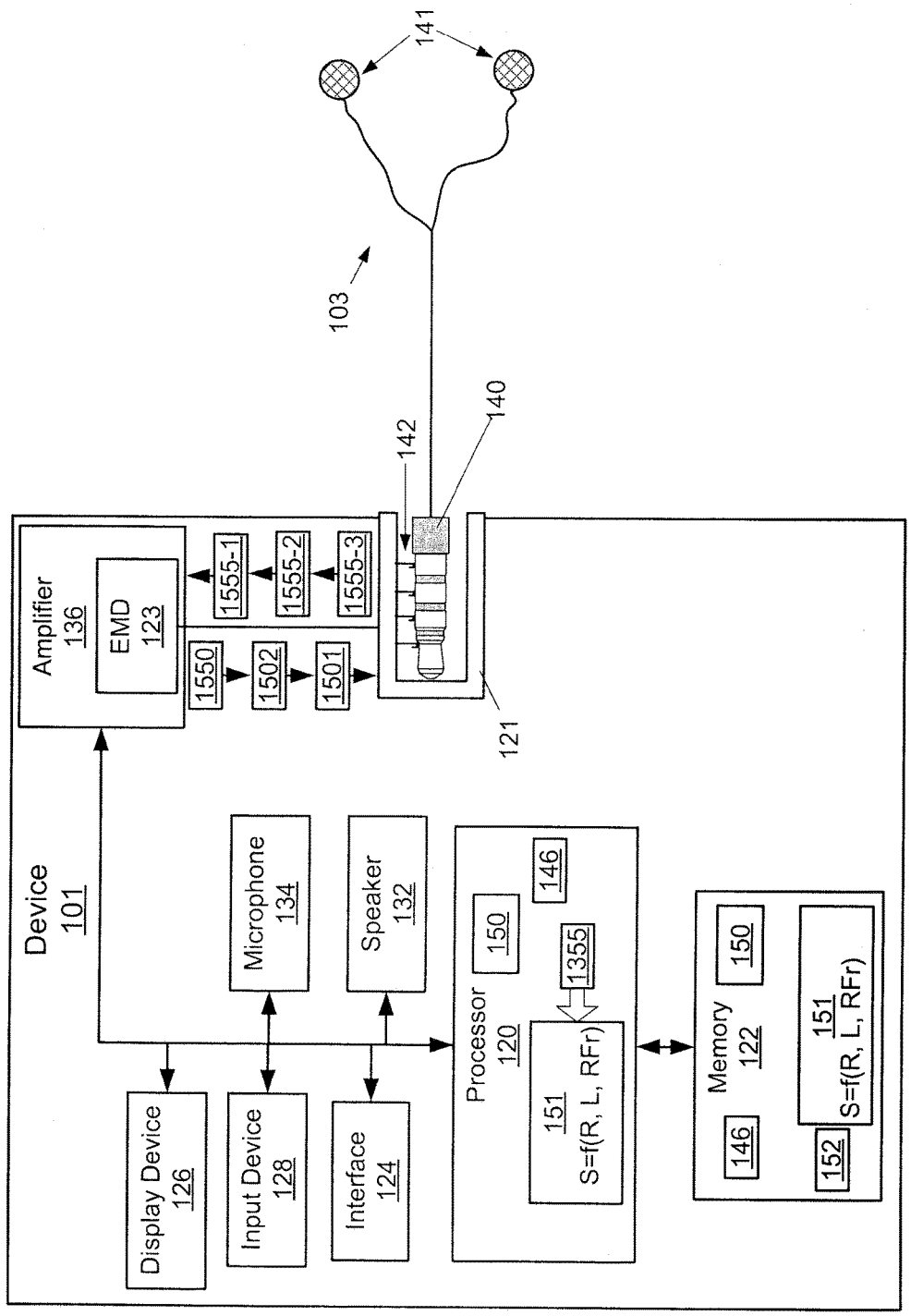
FIG. 15 depicts the device of FIG. 2 implementing a portion of the method of FIG. 3, according to alternative non-limiting implementations.

While FIG. 15 depicts EMD 123 receiving resistance 1555-1, impedance 1555-2 and resonance frequency 1555-3 from audio port 121, it is appreciated that each of resistance 1555-1, impedance 1555-2 and resonance frequency 1555-3 can represent data (for example inductance data) from which resistance, impedance and resonance frequency can be derived rather than a direct measurement.

Figure 5:
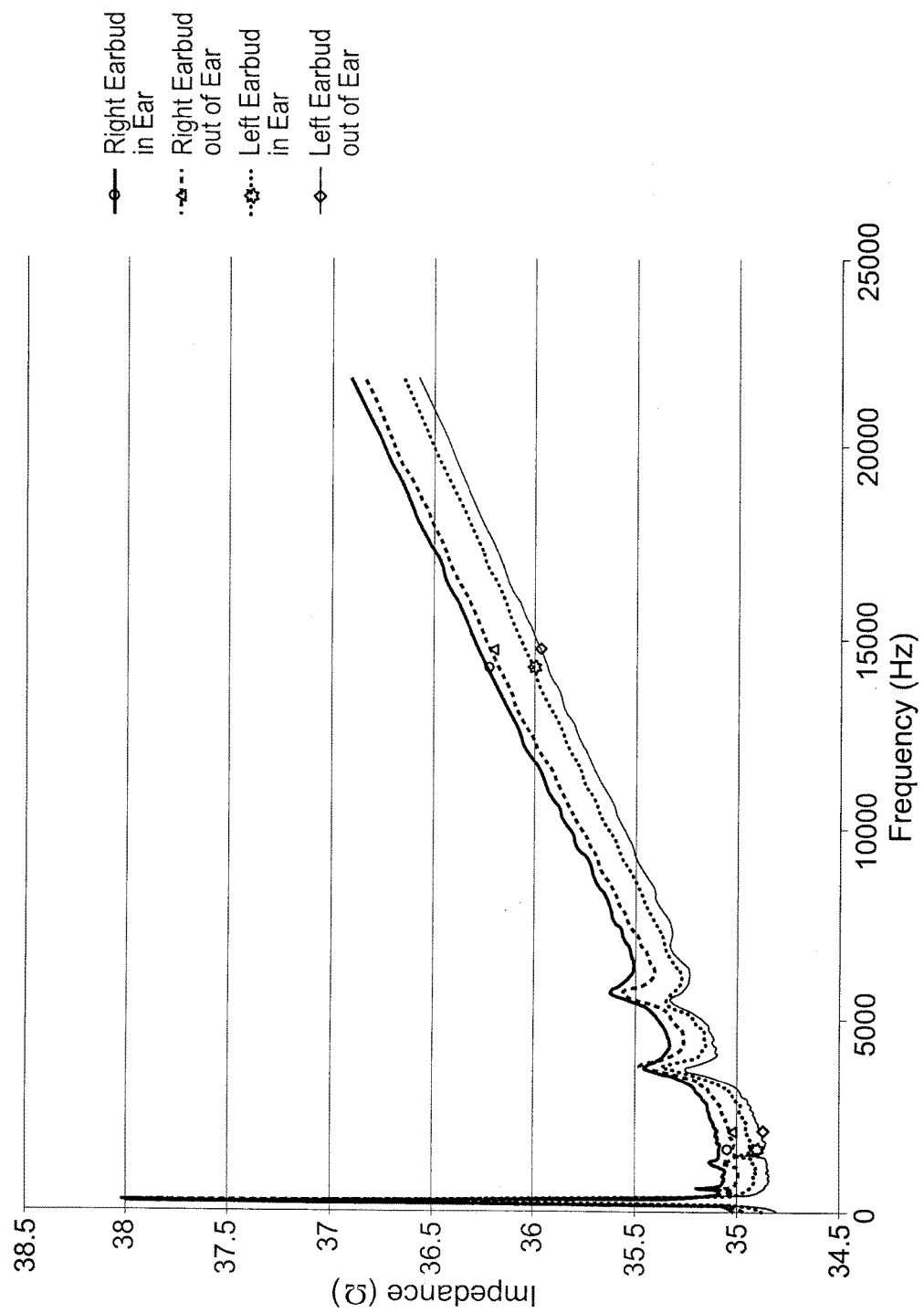
FIG. 5 depicts the impedance of FIG. 4 on a linear scale, according to non-limiting implementations.

For example, application 146 and/or data 150 can store sound data for playing each of first frequency tone 1501 and second frequency tone 1502, and, when block 303 is implemented at processor 120, such sound data is processed to produce first frequency tone 1501 and second frequency tone 1502. Furthermore, first frequency tone 1501 and second frequency tone 1502 (and audio data 1550) can be played in any order. In general a frequency of first frequency tone 1501 is selected to be in a range where resistance dominates an inductance response of headset 103, for example below 1000 Hz as shown in FIG. 4 and FIG. 5; similarly, a frequency of second frequency tone 1502 is selected to be in a range where impedance dominates an inductance response of headset 103, for example above 2000 Hz as shown in FIG. 4 and FIG. 5. Hence, as each of first frequency tone 1501 and second frequency tone 1502, and EMD 123 measures the resulting electrical properties, the electrical properties measured as first frequency tone 1501 is played being related to resistance, the electrical properties measured as second frequency tone 1502 is played being related to impedance.

As also depicted in FIG. 15, processor 120 can play audio data 1550 at audio port 121 in the frequency range of the human hearing system to measure a resonance frequency of the external device in the frequency range of the human hearing system. In some implementations, audio data 1550 can comprise special audio data which scans across the frequency range of the human hearing system. However, in other implementations, audio data 1550 can be similar to output 1350 and comprise music, and the like, stored in data 150. Either way, resonance frequency 1555-3 can comprise data similar to electrical properties 1355. Indeed, in implementations where audio data 1550 is similar to output 1350, further determinations of resistance and impedance can occur as described above with respect to FIG. 13 and FIG. 14.

Once resistance, impedance and resonance frequency are determined, sensitivity of headset 103 can be determined an output of amplifier 136 to audio port 121 can be adjusted as described above with reference to FIG. 14.

Hence, described herein is a device that can measure electrical properties of external devices plugged into an audio port and determine sensitivity of the external devices from the electrical properties. The output to the external device, and specifically sound output, can then be boosted or limited based on the determined sensitivity. In some implementations, the output to the external device can be adjusted to a given output level once the sensitivity is determined to limit the level of sound output at the external device. In particular such a determination can result in the sensitivity to be automatically adjusted to either boost the output, in instances where the sensitivity is low, or limit the output, in instances where the sensitivity it high. In the latter case, damage to a listener's ear can be obviated. Hence, present implementations further have ergonomic uses.

Those skilled in the art will appreciate that in some implementations, the functionality of device 101 can be implemented using pre-programmed hardware or firmware elements (e.g., application specific integrated circuits (ASICs), electrically erasable programmable read-only memories (EEPROMs), etc.), or other related components. In other implementations, the functionality of device 101 can be achieved using a computing apparatus that has access to a code memory (not depicted) which stores computer-readable program code for operation of the computing apparatus. The computer-readable program code could be stored on a computer readable storage medium which is fixed, tangible and readable directly by these components, (e.g., removable diskette, CD-ROM, ROM, fixed disk, USB drive). Furthermore, the computer-readable program can be stored as a computer program product comprising a computer usable medium. Further, a persistent storage device can comprise the computer readable program code. The computer-readable program code and/or computer usable medium can comprise a non-transitory computer-readable program code and/or non-transitory computer usable medium. Alternatively, the computer-readable program code could be stored remotely but transmittable to these components via a modem or other interface device connected to a network (including, without limitation, the Internet) over a transmission medium. The transmission medium can be either a non-mobile medium (e.g., optical and/or digital and/or analog communications lines) or a mobile medium (e.g., microwave, infrared, free-space optical or other transmission schemes) or a combination thereof.

A portion of the disclosure of this patent document contains material which is subject to copyright protection. The copyright owner has no objection to the facsimile reproduction by any one of the patent document or patent disclosure, as it appears in the Patent and Trademark Office patent file or records, but otherwise reserves all copyrights whatsoever.

Persons skilled in the art will appreciate that there are yet more alternative implementations and modifications possible, and that the above examples are only illustrations of one or more implementations. The scope, therefore, is only to be limited by the claims appended hereto.

What is claimed is:

1. A device comprising:
   a processor, an audio port, and an electrical measurement device configured to measure one or more electrical properties of an external device plugged into the audio port over a range of frequencies, the processor configured to:
      measure, using the electrical measurement device, the one or more electrical properties of the external device plugged into the audio port at a plurality of frequencies by:
         playing a first frequency tone at the audio port that is lower than a frequency range of a human hearing system, and measuring a resistance of the external device at first frequency tone;
         playing a second frequency tone at the audio port that is higher than the frequency range of the human hearing system, and measuring an inductance of the external device at second frequency tone; and
         playing audio data at the audio port in the frequency range of the human hearing system, and measuring a resonance frequency of the external device in the frequency range of the human hearing system;
      determine a sensitivity of the external device using: the resistance, the inductance and the resonance frequency of the external device; and a predetermined function that relates the sensitivity to the resistance, the inductance and the resonance frequency of the external device; and,
      adjust an output to the audio port based on the sensitivity.

2. The device of claim 1, wherein the electrical measurement device is configured to measure impedance of the external device plugged into the audio port over the range of frequencies, and the processor is further configured to measure the one or more electrical properties by measuring the impedance of the external device.

3. The device of claim 1, further comprising a memory storing the predetermined function.

4. The device of claim 1, wherein the processor is further configured to initiate measurement of the one or more electrical properties when the external device is plugged into the audio port.

5. The device of claim 1, further comprising a memory storing a given output level, and the processor is further configured to adjust the output to the audio port based on the sensitivity such that the output is less than or equal to the given output level.

6. The device of claim 1, wherein the processor is further configured to:
   play the output at an initial output level while one or more of measurement of the one or more electrical properties and determination of the sensitivity is occurring; and
   adjust the output to the audio port based on the sensitivity from the initial output level.

7. The device of claim 1, wherein the processor comprises a digital signal processor, the electrical measurement device comprises a component of an amplifier, and the audio port comprises one of a 3.5 mm audio plug or a 2.5 mm audio plug.

8. A method comprising:
   at a device comprising: processor, an audio port, and an electrical measurement device configured to measure one or more electrical properties of an external device plugged into the audio port over a range of frequencies,
   measuring, using the electrical measurement device, the one or more electrical properties of the external device plugged into the audio port at a plurality of frequencies by:
      playing a first frequency tone at the audio port that is lower than a frequency range of a human hearing system, and measuring a resistance of the external device at first frequency tone;
      playing a second frequency tone at the audio port that is higher than the frequency range of the human hearing system, and measuring an inductance of the external device at second frequency tone; and
      playing audio data at the audio port in the frequency range of the human hearing system, and measuring a resonance frequency of the external device in the frequency range of the human hearing system;
   determining, using the processor, a sensitivity of the external device using: the resistance, the inductance and the resonance frequency of the external device, measured using the electrical measurement device; and a predetermined function that relates the sensitivity to the resistance, the inductance and the resonance frequency of the external device; and,
   adjusting, using the processor, an output to the audio port based on the sensitivity.

9. The method of claim 8, wherein the electrical measurement device is configured to measure impedance of the external device plugged into the audio port over the range of frequencies, and the method further comprises measuring the one or more electrical properties by measuring the impedance of the external device.

10. The method of claim 8, wherein the device further comprises a memory storing the predetermined function.

11. The method of claim 8, further comprising initiating measurement of the one or more electrical properties when the external device is plugged into the audio port.

12. The method of claim 8, wherein the device further comprises a memory storing a given output level, and the method further comprises adjusting the output to the audio port based on the sensitivity such that the output is less than or equal to the given output level.

13. The method of claim 8, wherein the method further comprises:
  playing the output at an initial output level while one or more of measurement of the one or more electrical properties and determination of the sensitivity is occurring; and
  adjusting the output to the audio port based on the sensitivity from the initial output level.

14. A non-transitory computer-readable medium storing a computer program, wherein execution of the computer program is for:
  at a device comprising: processor, an audio port, and an electrical measurement device configured to measure electrical properties of an external device plugged into the audio port over a range of frequencies, measuring, using the electrical measurement device, one or more electrical properties of the external device plugged into the audio port at a plurality of frequencies by:
    playing a first frequency tone at the audio port that is lower than a frequency range of a human hearing system, and measuring a resistance of the external device at first frequency tone;
    playing a second frequency tone at the audio port that is higher than the frequency range of the human hearing system, and measuring an inductance of the external device at second frequency tone; and
    playing audio data at the audio port in the frequency range of the human hearing system, and measuring a resonance frequency of the external device in the frequency range of the human hearing system;
  determining, using the processor, a sensitivity of the external device using: the resistance, the inductance and the resonance frequency of the external device measured using the electrical measurement device; and a predetermined function that relates the sensitivity to the resistance, the inductance and the resonance frequency of the external device; and,
  adjusting, using the processor, an output to the audio port based on the sensitivity.

* * * * *